(12) United States Patent
Shinya et al.

(10) Patent No.: US 8,877,878 B2
(45) Date of Patent: Nov. 4, 2014

(54) EPOXY RESIN COMPOSITION WITH SULFONIUM BORATE COMPLEX

(75) Inventors: Yoshihisa Shinya, Tochigi (JP); Jun Yamamoto, Tochigi (JP); Ryota Aizaki, Tochigi (JP); Naoki Hayashi, Tochigi (JP); Misao Konishi, Tochigi (JP); Yasuhiro Fujita, Tochigi (JP)

(73) Assignee: Dexerials Corporation, Tokyo (JP)

( * ) Notice: Subject to any disclaimer, the term of this patent is extended or adjusted under 35 U.S.C. 154(b) by 319 days.

(21) Appl. No.: 13/123,369

(22) PCT Filed: Dec. 2, 2009

(86) PCT No.: PCT/JP2009/070222
§ 371 (c)(1),
(2), (4) Date: Apr. 8, 2011

(87) PCT Pub. No.: WO2010/064648
PCT Pub. Date: Jun. 10, 2010

(65) Prior Publication Data
US 2011/0192639 A1 Aug. 11, 2011

(30) Foreign Application Priority Data
Dec. 5, 2008 (JP) ................. 2008-310827

(51) Int. Cl.
| | | |
|---|---|---|
| B01J 31/14 | (2006.01) |
| C08G 59/72 | (2006.01) |
| C08L 63/00 | (2006.01) |
| C08L 63/02 | (2006.01) |
| C08L 63/04 | (2006.01) |
| H01L 23/00 | (2006.01) |
| H05K 1/02 | (2006.01) |
| C07F 5/02 | (2006.01) |
| C08G 59/68 | (2006.01) |
| C07C 381/12 | (2006.01) |

(52) U.S. Cl.
CPC ............ *C07F 5/027* (2013.01); *C08L 63/00* (2013.01); *C08G 59/687* (2013.01); *C07C 381/12* (2013.01)
USPC .......... 525/523; 174/259; 257/783; 502/155; 525/480

(58) Field of Classification Search
None
See application file for complete search history.

(56) References Cited

U.S. PATENT DOCUMENTS

| | | | |
|---|---|---|---|
| 5,468,902 A | 11/1995 | Castellanos et al. |
| 5,550,265 A | 8/1996 | Castellanos et al. |
| 5,668,192 A | 9/1997 | Castellanos et al. |
| 6,147,184 A | 11/2000 | Castellanos et al. |
| 6,153,661 A | 11/2000 | Castellanos et al. |
| 6,861,455 B2 * | 3/2005 | Hayashi .......................... 522/25 |

FOREIGN PATENT DOCUMENTS

| | | | |
|---|---|---|---|
| JP | A-3-237107 | | 10/1991 |
| JP | A-4-1177 | | 1/1992 |
| JP | A-6-184170 | | 7/1994 |
| JP | 9-176112 A | * | 7/1997 |
| JP | A-9-176112 | | 7/1997 |
| JP | A-10-245378 | | 9/1998 |
| JP | A-10-310587 | | 11/1998 |
| JP | A-2006-96742 | | 4/2006 |
| WO | WO 2008/149592 A1 | | 11/2008 |
| WO | WO 2008/152843 A1 | | 12/2008 |

OTHER PUBLICATIONS

HCAPLUS accession No. 2010:721132 for U.S. Publication No. 2011/0192639 (the publication of the instant application), Shinya et al., Aug. 11, 2011, two pages.*
Toba et al., "Design of Photoinitiator With Onium Borate," Japanese Journal of Polymer Science and Technology, vol. 59, Issue 8, 2002, pp. 449-459, English translation.*
Chemical abstracts registry No. 141651-31-2 for Sanaid SI 80L, 2001, one page.*
International Preliminary Report on Patentability issued in International Patent Application No. PCT/JP2009/07022 dated Jul. 5, 2011 (with translation).
Toba et al., "Cationic Photopolymerization of Epoxides by Direct and Sensitized Photolysis of Onium Tetrakis(pentaflurophenyl)borate Initiators," Macromolecules, 1999, pp. 3209-3215, vol. 32.
International Search Report mailed Dec. 28, 2009 issued in International Application No. PCT/JP2009/070222 (with translation).
Aug. 23, 2012 Taiwanese Office Action issued in Taiwanese Patent Application No. 98141469 (with translation).
Jan. 15, 2013 Extended European Search Report issued in European Patent Application No. 09830414.0.
Sep. 4, 2013 Notification of Reason(s) for Refusal issued in Japanese Patent Application No. 2008-310827 (with translation).
Jun. 4, 2013 Office Action issued in Taiwanese Patent Application No. 98141469 (with English-language translation).
Mar. 4, 2013 Office Action issued in Chinese Patent Application No. 200980149017.0 (with translation).
Dec. 31, 2013 Office Action issued in Chinese Patent Application No. 200980149017.0.
Nov. 5, 2013 Office Action issued in European Patent Application No. 09830414.0.

* cited by examiner

*Primary Examiner* — Robert Sellers
(74) *Attorney, Agent, or Firm* — Oliff PLC

(57) ABSTRACT

A sulfonium borate complex that is capable of reducing the amount of fluorine ions generated during thermal cationic polymerization, and is capable of providing a thermal cationic polymerizable adhesive with low-temperature fast curing properties is represented by a structure represented by the formula (1).

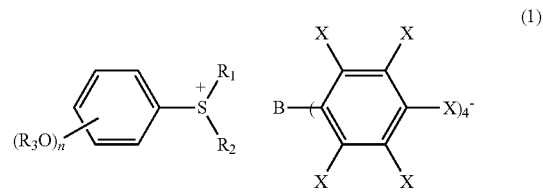

In the formula (1), $R_1$ is an aralkyl group, $R_2$ is a lower alkyl group, and $R_3$ is a lower alkoxycarbonyl group. X is a halogen atom, and n is an integer of from 1 to 3.

2 Claims, 5 Drawing Sheets

EPOXY RESIN COMPOSITION WITH SULFONIUM BORATE COMPLEX

TECHNICAL FIELD

The present invention relates to a sulfonium borate complex useful as a thermal cationic polymerization initiator, a method for producing the complex, an epoxy resin composition containing the complex, and a connection structure using the composition.

BACKGROUND ART

Conventionally, a photocationic polymerizable adhesive containing an epoxy resin as a main component has been used as a kind of adhesive used for mounting an electronic part such as an IC chip on a wiring board. Such a photocationic polymerizable adhesive has been formulated with a photocationic polymerization initiator that initiates cationic polymerization by generating protons via light. A sulfonium antimonate complex is known as such a photocationic polymerization initiator.

A sulfonium antimonate complex, however, has as a counter anion $SbF_6^-$ having fluorine atoms bonded to a metallic antimony, thereby causing a problem of producing large amounts of fluorine ions during cationic polymerization to corrode a metal wiring and a connection pad. Thus, it has been suggested that a sulfonium borate complex with a tetrakis(pentafluorophenyl)borate anion $[(C_6F_5)_4B^-]$ having fluorine atoms bonded to carbon atoms instead of $SbF_6^-$ is used as a cationic polymerization initiator (Patent Document 1). In fact, the complex, [p-hydroxyphenyl-benzyl-methylsulfonium tetrakis(pentafluorophenyl)borate], of the following formula (1c) is commercially available.

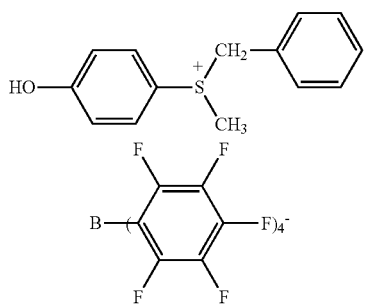

(1c)

Actually, a joining portion cannot be irradiated with light in many cases when an electronic part is mounted on a wiring board. Thus, an attempt has been made to divert the specific sulfonium borate complex disclosed in Examples of Patent Document 1 to a thermal cationic polymerization initiator for a thermal cationic polymerizable adhesive. In such a case, it is desirable that the amount of fluorine ions generated during cationic polymerization be reduced to improve not only electrolytic corrosion resistance but also low-temperature fast curing properties of a thermal cationic polymerizable adhesive for productivity improvement.

CITATION LIST

Patent Literature

[Patent Document 1] Japanese Patent Application Laid-open No. Hei 9-176112

DISCLOSURE OF THE INVENTION

Problems that the Invention is to Solve

The use of the complex of the formula (1c) as a thermal cationic polymerization initiator reduced the amount of fluorine ions generated during thermal cationic polymerization to some extent, but did not provide sufficient low-temperature fast curing properties to an epoxy resin composition for a thermal cationic polymerizable adhesive.

The present invention addresses the above-mentioned problems of the conventional technique. Accordingly, it is an object of the present invention to provide a sulfonium borate complex that can reduce the amount of fluorine ions generated during thermal cationic polymerization to improve electrolytic corrosion resistance, and moreover can provide low-temperature fast curing properties to an epoxy resin composition for a thermal cationic polymerizable adhesive.

Means for Solving the Problem

The present inventors have found that the above-mentioned object can be achieved by introducing a combination of a plurality of specific substituents into the sulfonium residue of a sulfonium borate complex, thereby completing the present invention.

Specifically, the present invention is a sulfonium borate complex represented by the formula (1).

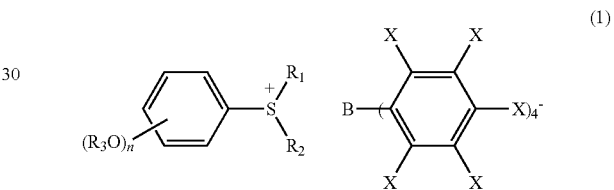

(1)

In the formula (1), $R_1$ is an aralkyl group, $R_2$ is a lower alkyl group, and $R_3$ is a lower alkoxycarbonyl group. X is a halogen atom, and n is an integer of from 1 to 3.

The present invention is also a method for producing the sulfonium borate complex of the formula (1), wherein the sulfonium borate complex is obtained by the reaction of a sulfonium antimonate complex of the formula (2) with a sodium borate salt of the formula (3).

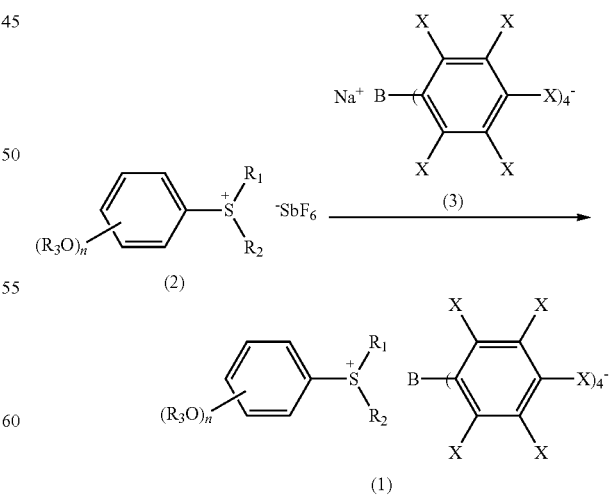

In the formula (1), (2), or (3), $R_1$ is an aralkyl group, $R_2$ is a lower alkyl group, and $R_3$ is a lower alkoxycarbonyl group. X is a halogen atom, and n is an integer of from 1 to 3.

The present invention also provides an epoxy resin composition composed of an epoxy resin and a thermal cationic polymerization initiator, characterized in that the thermal cationic polymerization initiator is the sulfonium borate complex represented by the formula (1) described above. In addition, the present invention provides a connection structure characterized in that an electronic part is joined to a wiring board with a thermosetting product of the epoxy resin composition.

Effects of the Invention

The sulfonium borate complex of the formula (1) according to the present invention has a combination of a plurality of substituents. Thus, during thermal cationic polymerization of the epoxy resin composition, in which the complex is contained as a thermal cationic polymerization initiator for a thermal cationic adhesive, the amount of generated fluorine ions can be reduced to improve electrolytic corrosion resistance and moreover provide low-temperature fast curing properties.

BEST MODE FOR CARRYING OUT THE INVENTION

Figure 1:
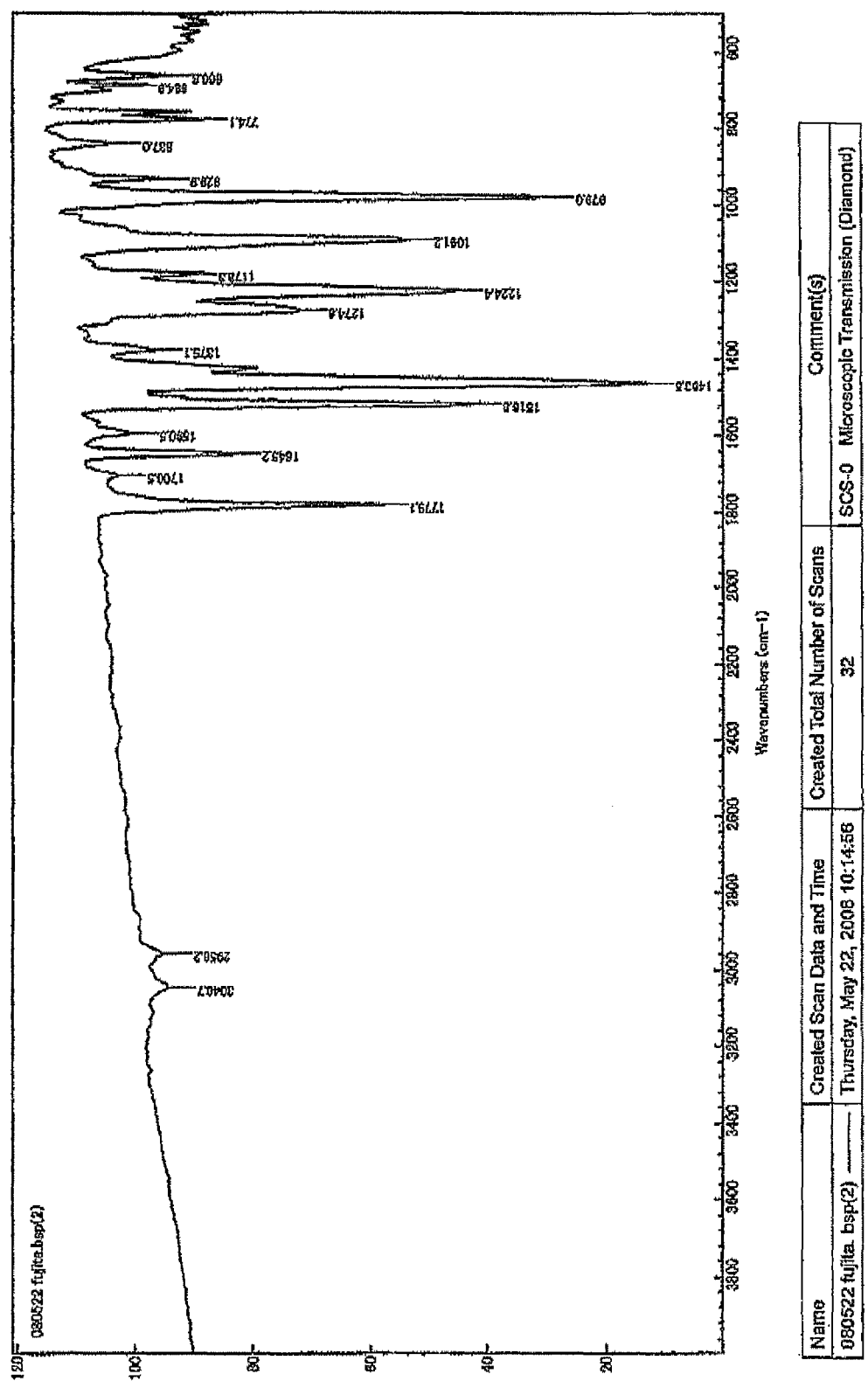
FIG. 1 is an IR chart of the sulfonium borate complex of Example 1.

A compound according to the present invention is the sulfonium borate complex represented by the formula (1).

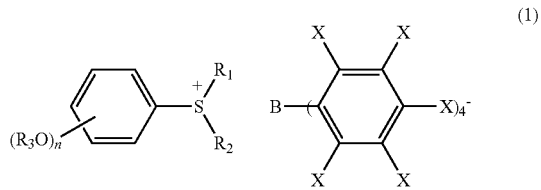

(1)

In the formula (1), examples of the aralkyl group $R_1$ include a benzyl group, an o-methylbenzyl group, a (1-naphthyl)methyl group, a pyridylmethyl group, an anthracenylmethyl group, and the like. Among them, an o-methylbenzyl group is preferred in terms of favorable rapid curing properties and ease of availability.

Examples of the lower alkyl group $R_2$ include a methyl group, an ethyl group, a propyl group, a butyl group, and the like. Among them, a methyl group is preferred in terms of favorable rapid curing properties and ease of availability.

The number of hydroxyl groups of the phenyl group bonded to the sulfonium residue, that is, n is an integer of from 1 to 3. Examples of such a phenyl group, when n is 1, include a 4-(lower alkoxycarbonyloxy)phenyl group, 2-(lower alkoxycarbonyloxy)phenyl group, and a 3-(lower alkoxycarbonyloxy)phenyl group, and the like. Examples of such a phenyl group, when n is 2, include a 2,4-di(lower alkoxycarbonyloxy)phenyl group, a 2,6-di(lower alkoxycarbonyloxy)phenyl group, a 3,5-di(lower alkoxycarbonyloxy)phenyl group, a 2,3-di(lower alkoxycarbonyloxy)phenyl group, and the like. Examples of such a phenyl group, when n is 3, include a 2,4,6-tri(lower alkoxycarbonyloxy)phenyl group, a 2,4,5-tri(lower alkoxycarbonyloxy)phenyl group, a 2,3,4-tri(lower alkoxycarbonyloxy)phenyl group, and the like. Among them, a 4-(lower alkoxycarbonyloxy)phenyl group wherein n is 1, in particular, a 4-methoxycarbonyloxyphenyl group, is preferred in terms of favorable rapid curing properties and ease of availability.

Examples of the halogen atom X include a fluorine atom, a chlorine atom, a bromine atom and an iodine atom. Among them, a fluorine atom is preferred due to its high electron-withdrawing ability to improve reactivity.

The sulfonium borate complex of the formula (1) according to the present invention can be produced in accordance with the following reaction formula. Here, for each substituent in the formula (1), (2) or (3), as described above, $R_1$ is an aralkyl group, $R_2$ is a lower alkyl group, and $R_3$ is a lower alkoxycarbonyl group. X is a halogen atom, and n is an integer of from 1 to 3.

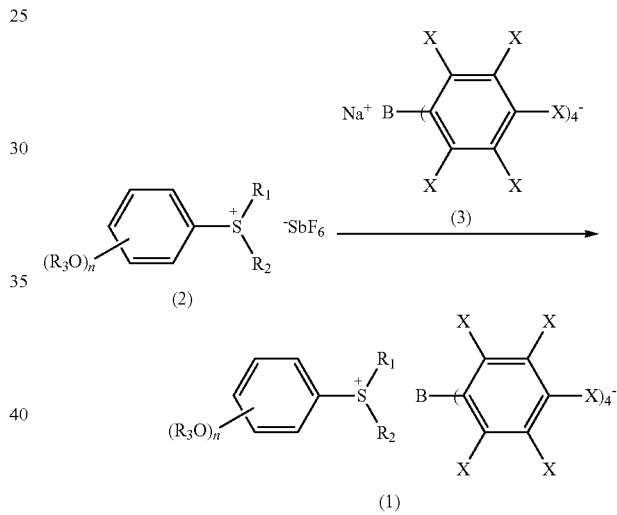

Namely, the sulfonium antimonate complex of the formula (2) (see Japanese Patent Application Laid-Open No. 2006-96742 for the synthesis method) was dissolved in an organic solvent such as ethyl acetate. The resulting solution was then mixed with an aqueous solution of the sodium borate salt of the formula (3) (see Japanese Patent Application Laid-Open No. Hei 10-310587 for the synthesis method) in an equimolar amount. The obtained two-layer system mixture was stirred at a temperature of from 20° C. to 80° C. for one to three hours to react the sulfonium antimonate complex of the formula (2) with the sodium borate salt of the formula (3), thereby obtaining the sulfonium borate complex of the formula (1). (According to Japanese Patent Application Laid-Open No. 2006-96742, the sulfonium borate complex of the formula (2), specifically, may be synthesized by reacting a hydroxyphenyl sulfonium antimonate complex, corresponding to a compound of the complex of the formula (2) with a formate residue removed, with a lower alkyl chloroformate compound (such as methyl chloroformate) in acetonitrile in the presence of triethylamine.) Isolation of the sulfonium borate complex of the formula (1) can be achieved by separating and drying an organic solvent layer and then removing an organic solvent through evaporation under reduced pressure to give the target product as an evaporation residue.

The sulfonium borate complex of the formula (1) according to the present invention can be used as a thermal cationic polymerization initiator for a general epoxy resin such as a thermal cationic polymerizable adhesive. Accordingly, the epoxy resin composition that is formulated with an epoxy resin and the sulfonium borate complex of the formula (1) according to the present invention as a thermal cationic polymerization initiator is also a part of the present invention.

A thermosetting epoxy resin that is conventionally used for joining electronic materials can be used appropriately as an epoxy resin constituting the epoxy resin composition according to the present invention. Such a thermosetting epoxy resin may be either in liquid form or in solid form, and normally has an epoxy equivalent weight of from 100 to 4000, preferably two or more epoxy groups per molecule. For example, a bisphenol A epoxy compound, a phenol novolac epoxy compound, a cresol novolac epoxy compound, an ester epoxy compound, an alicyclic epoxy compound, and the like can be preferably used. These compounds also include monomers and oligomers thereof.

The curing of the epoxy resin composition according to the present invention is insufficient when the formulated amount of the sulfonium borate complex of the formula (1) with respect to 100 parts by mass of epoxy resin is too small, whereas the storage stability thereof is decreased when it is too large. Therefore, the formulated amount of the sulfonium borate complex in the epoxy resin composition is preferably from 0.1 to 10 parts by mass, and more preferably, from 0.5 to 5 parts by mass with respect to 100 parts by mass of epoxy resin.

In the epoxy resin composition according to the present invention, in addition to the thermosetting epoxy resin described above, another thermosetting resin such as a thermosetting urea resin, a thermosetting melamine resin, and a thermosetting phenol resin, and a thermoplastic resin such as a polyester resin, and a polyurethane resin can be used together as long as it does not hinder the effects of the invention.

The epoxy resin composition according to the present invention may contain a filler such as silica and mica, a pigment, an antistatic agent, a silane coupling agent, and the like if desired. The epoxy resin composition according to the present invention may be used in the form of a solution in a solvent such as toluene, a paste, a deposited film, and the like.

The epoxy resin composition according to the present invention can be produced by uniformly mixing an epoxy resin and a thermal cationic polymerization initiator with, if desired, other additives such as a silane coupling agent, a thermosetting resin, and a filler under stirring in accordance with a conventional method.

Thus, in the resulting epoxy resin composition according to the present invention, the sulfonium borate complex is used as a thermal cationic polymerization initiator. Therefore, the amount of generated fluorine ions can be reduced during thermal cationic polymerization to improve electrolytic corrosion resistance and furthermore provide low-temperature fast curing properties.

Therefore, the epoxy resin composition according to the present invention can be preferably applied when an electronic part is mounted on a wiring board. Such a case provides a connection structure with good electrolytic corrosion resistance, in which an electronic part is joined to a wiring board with a thermosetting product of the epoxy resin composition. This connection structure is also a part of the present invention.

Examples of the wiring board include a flexible printed board, a glass epoxy substrate, a glass substrate, a tape substrate, and the like. Examples of the electronic part include an IC Chip, a resistor element, a capacitor element, an antenna element, a switching element, and the like.

Thermal cationic polymerization of the epoxy resin composition (in the form of a paste, a film, and the like) according to the present invention can be accomplished by heating at from 100° C. to 250° C.

EXAMPLES

Example 1 and Comparative Examples 1 to 3

The sulfonium antimonate complexes of the formulae (2a) to (2d) (see Japanese Patent Application Laid-Open No. Hei 10-245378 and No. 2006-96742 for the synthesis method) were dissolved in ethyl acetate to prepare 10 mass % of ethyl acetate solutions of the complexes, respectively. Separately, 10 mass % of aqueous solution of the sodium borate salt of the formula (3) (see Japanese Patent Application Laid-Open No. Hei 10-310587 for the synthesis method) was prepared.

Next, the 10 mass % of ethyl acetate solutions of the complexes were mixed with the 10 mass % of aqueous solution of the sodium borate salt of the formula (3) in an equimolar amount at room temperature, and stirred for 30 minutes. The ethyl acetate layers were then separated from the reaction mixtures respectively and dried, and ethyl acetate was removed under reduced pressure to obtain the sulfonium borate complex of the formula (1A) in Example 1 and the sulfonium borate complexes of the formulae (1a) to (1c) in Comparative Examples 1 to 3 as evaporation residues.

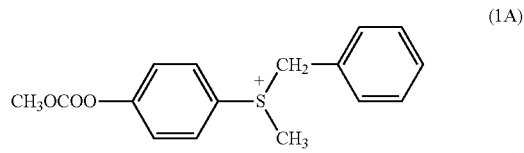

(1A)

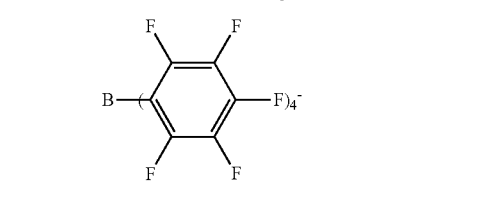

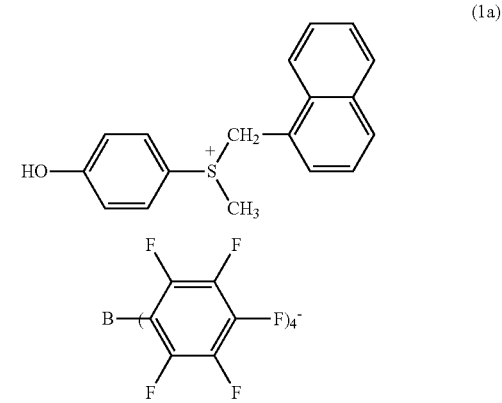

(1a)

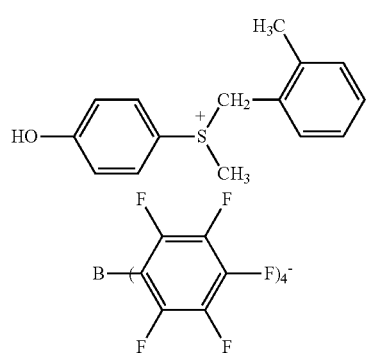 (1b)

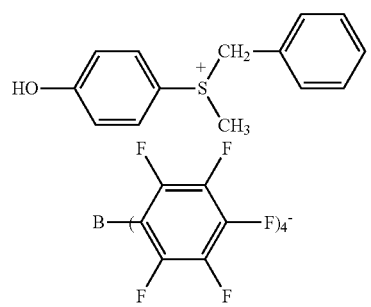 (1c)

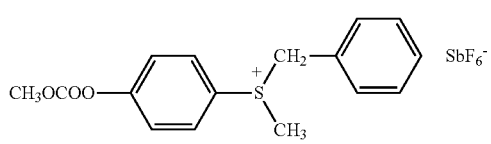 (2a)

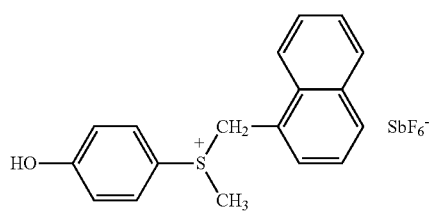 (2b)

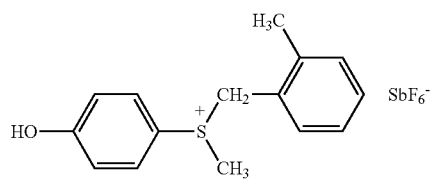 (2c)

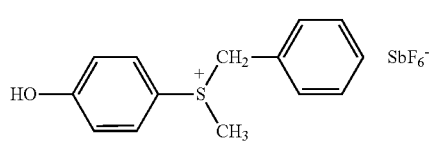 (2d)

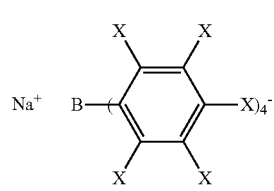 (3)

The compound, the sulfonium borate complex of the formula (1A) in Example 1, and each of the sulfonium borate complexes of the formulae (1a) and (1b) in Comparative Examples 1 and 2 were subjected to mass spectroscopy (instrument: AQUITY UPLC System, Waters Corporation), elemental analysis (instrument: PHOENIX, AMETEK Co., Ltd), IR analysis (instrument: 7000e FT-IR, Varian, Inc.), and $^1$H-NMR analysis (instrument: MERCURY PLUS, Varian, Inc.). According to the obtained results, these sulfonium borate complexes were confirmed to be the target compounds.

(i) Analysis results of the sulfonium borate complex, [p-methoxycarbonyloxyphenyl-benzyl-methylsulfonium tetrakis(pentafluorophenyl)borate], of the formula (1A) in Example 1

Figure 2A:
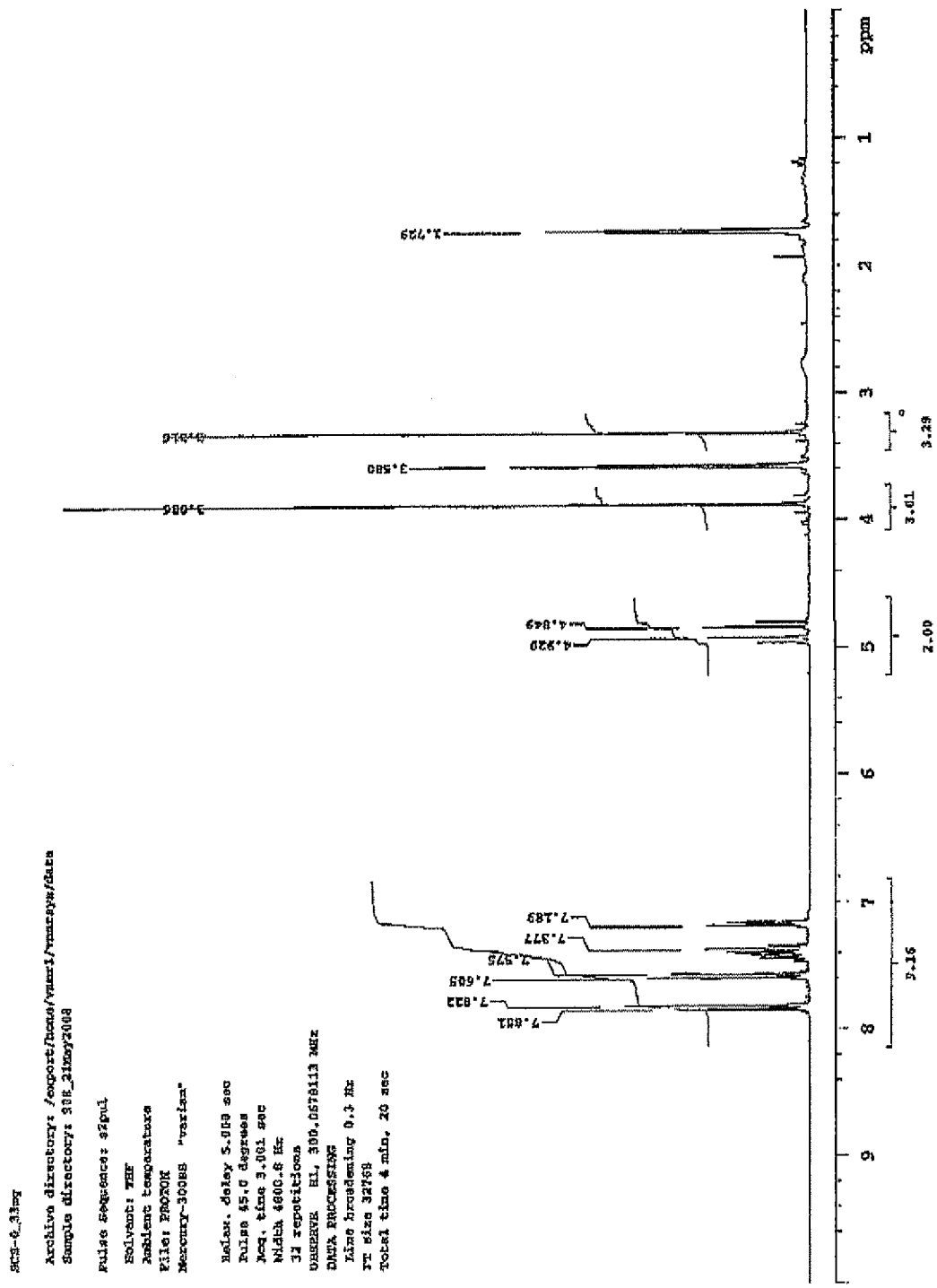
FIG. 2A is a $^1$H-NMR chart of the sulfonium borate complex of Example 1.
Figure 2B:
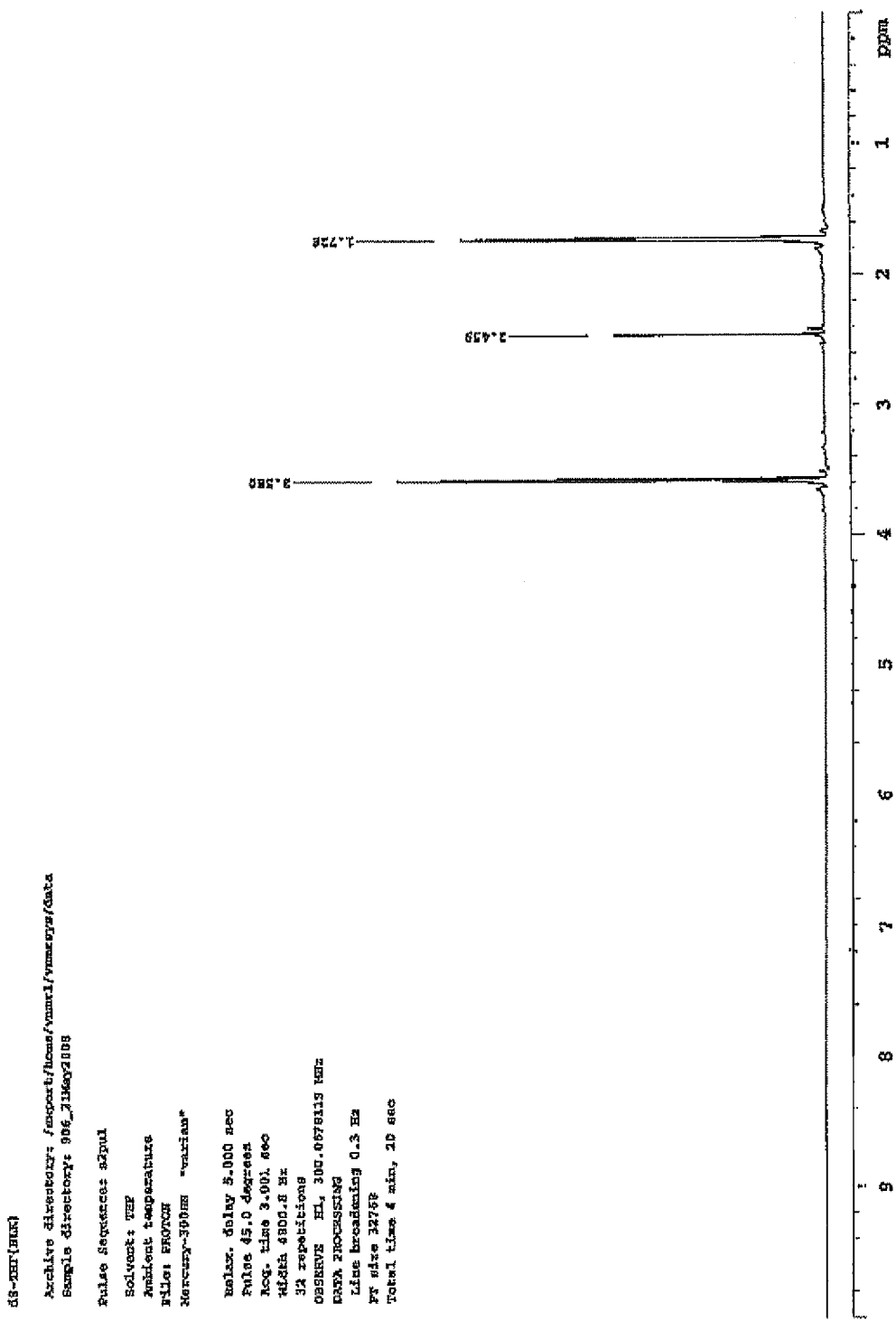
FIG. 2B is a $^1$H-NMR chart of THF.

<Results of MS Analysis>
$M^+$=289 (sulfonium residue)
$M^+$=679 (borate residue)
<Results of Elemental Analysis>
The measured values were in agreement with the theoretical values.
<Results of IR Analysis (cm$^{-1}$)>
The IR chart of the measurement results is shown in FIG. 1. The IR characteristic absorptions for bonds of the sulfonium borate complex of the formula (1A) in Example 1 were observed in the IR chart of FIG. 1.
<Results of $^1$H-NMR Analysis (δ Value)>
The $^1$H-NMR chart of the measurement results is shown in FIG. 2A, and the $^1$H-NMR chart of a solvent THF as a control is shown in FIG. 2B. The following protons were assigned in the $^1$H-NMR chart of FIG. 2A.

(Proton Assignments)

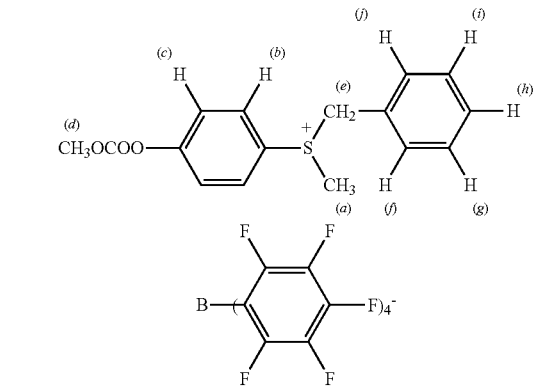

(ii) Analysis results of the sulfonium borate complex, [4-hydroxyphenyl-methyl-1-naphthylmethylsulfonium tetrakis(pentafluorophenyl)borate], of the formula (1a)

<Results of MS Analysis>
$M^+$=281 (sulfonium residue)
$M^+$=679 (borate residue)
<Results of Elemental Analysis>
Measured values C, 52.51; H, 1.89
Theoretical values C, 52.52; H, 1.78
<Results of IR Analysis (cm$^{-1}$)>
662 (C—S), 776, 980, 1088, 1276 (Ar—F), 1300, 1374, 1464, 1514, 1583, 1643, 2881 (C—H), 2981 (C—H), 3107 (O—H)

Figure 3:
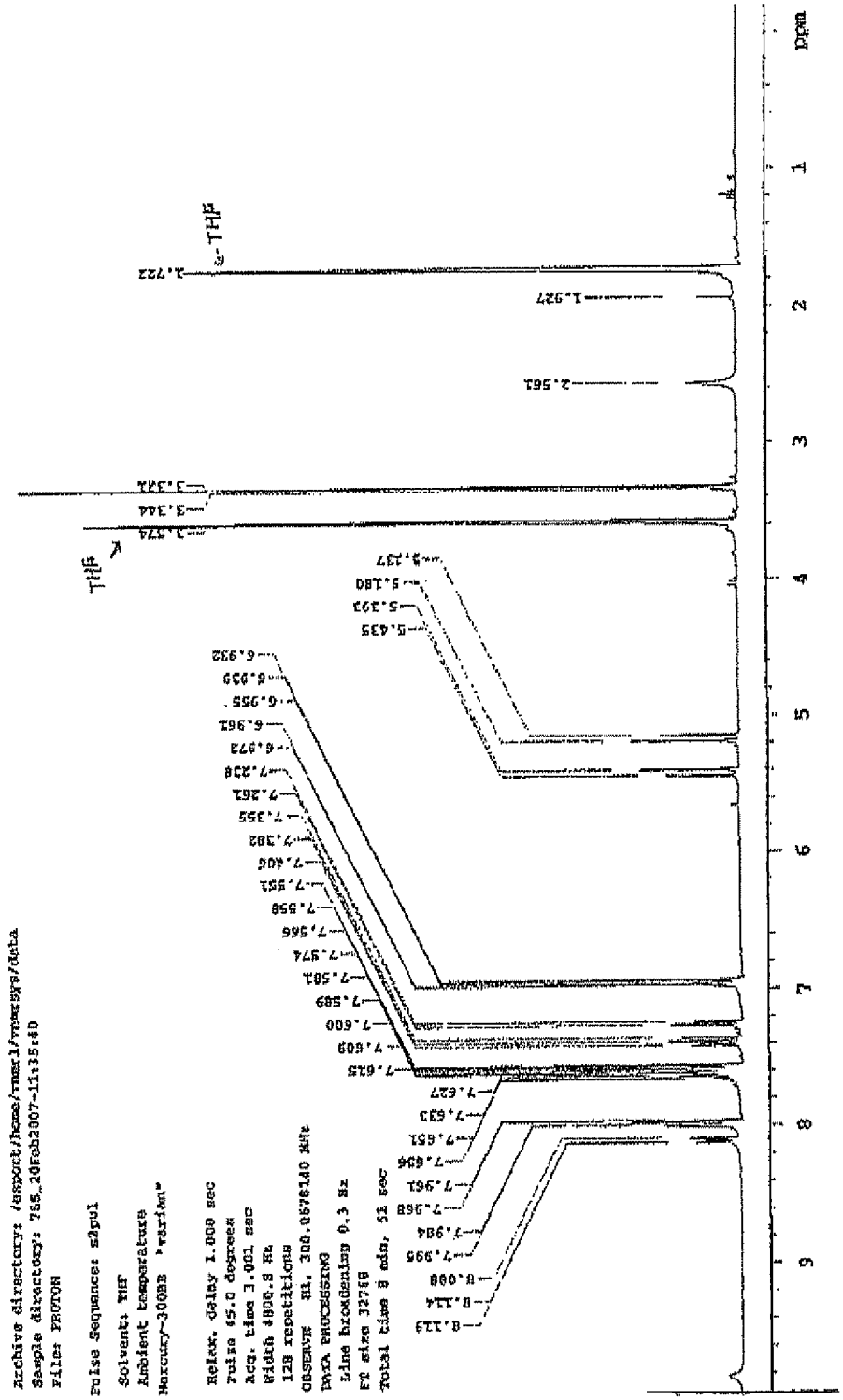
FIG. 3 is a $^1$H-NMR chart of the sulfonium borate complex of Comparative Example 1.

<Results of ¹H-NMR Analysis (δ Value), see FIG. 3 (with THF)>
2.6 (1H, (d)), 3.3 (3H, (a)), 5.3 (2H, (e)), 6.9 (2H, (c)), 7.6 (2H, (b)), 7.2-8.1 (7H, (f), (g), (h), (i), (j), (k), (l))

(Proton Assignments)

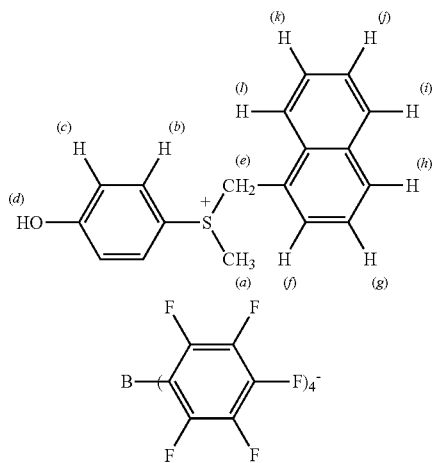

(iii) Analysis results of the sulfonium borate complex, [4-hydroxyphenyl-methyl-(2-methylbenzyl) sulfonium tetrakis(pentafluorophenyl)borate], of the formula (1b)

Figure 4:
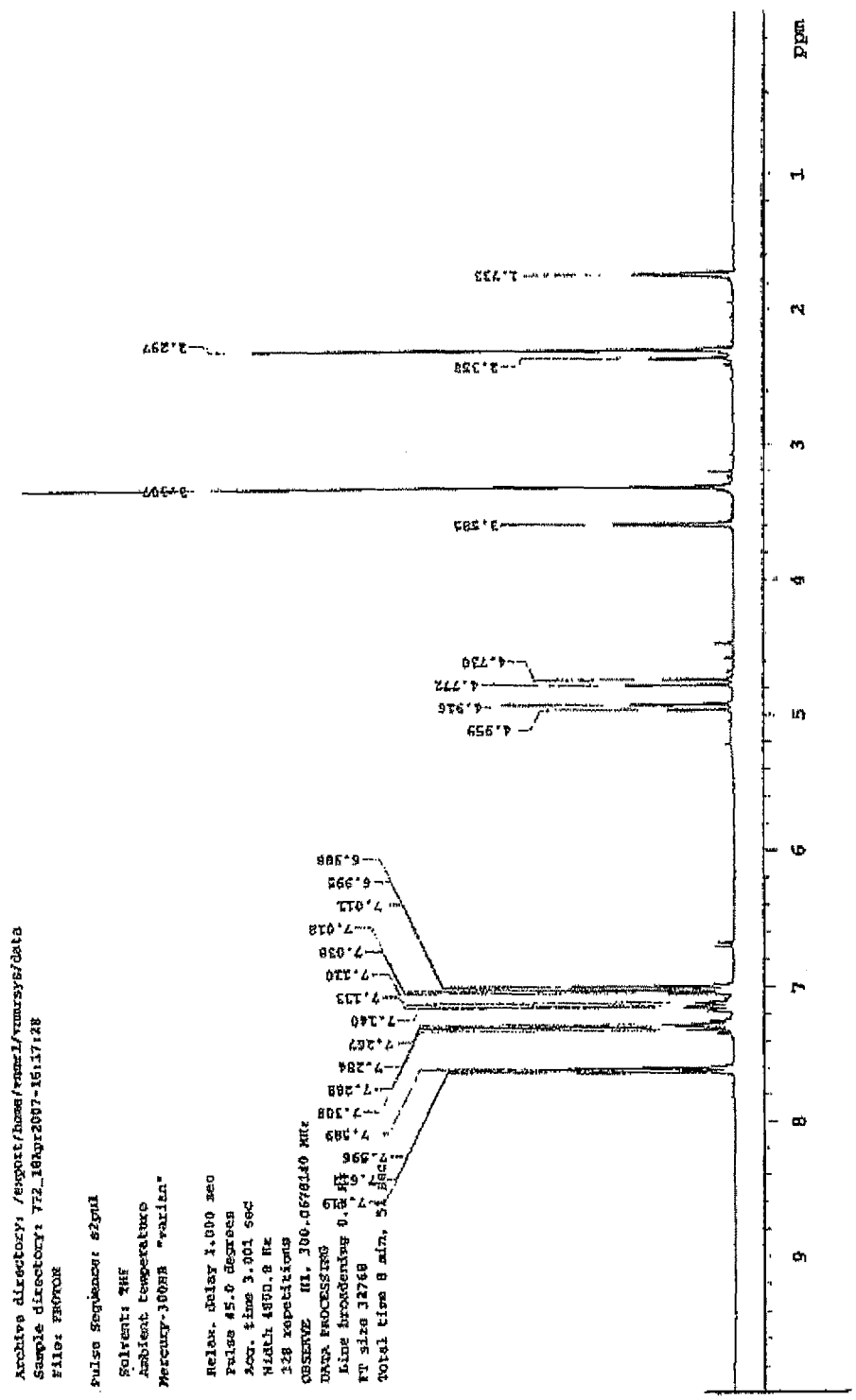
FIG. 4 is a $^1$H-NMR chart of the sulfonium borate complex of Comparative Example 2.

<Results of MS Analysis>
M⁺=245 (sulfonium residue)
M⁺=679 (borate residue)
<Results of Elemental Analysis>
Measured values C, 50.39; H, 1.77
Theoretical values C, 50.60; H, 1.80
<Results of IR Analysis (cm⁻¹)>
662 (C—S), 773, 980, 1088, 1276 (Ar—F), 1463, 1514, 1583, 1644, 2882 (C—H), 2983 (C—H), 3109 (O—H)
<Results of ¹H-NMR Analysis (δ Value), see FIG. 4 (with THF)>
2.3 (3H, (j)), 2.4 (1H, (d)), 3.3 (3H, (a)), 4.8 (2H, (e)), 7.0 (2H, (c)), 7.6 (2H, (b)), 7.0-7.4 (4H, (f), (g), (h), (i))

(Proton Assignments)

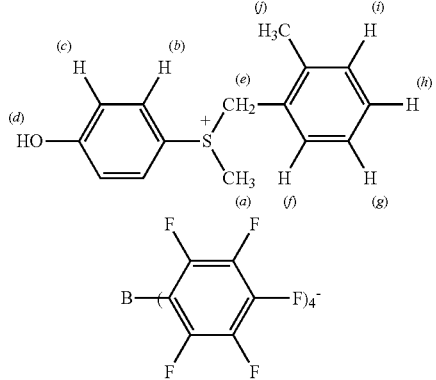

<Characteristic Evaluation>
Each of the sulfonium borate complexes (1A), (1a), (1b), and (1c) in Example 1 and Comparative Examples 1 to 3, and each of the sulfonium antimonate complexes (2a) to (2d) used therein as Reference Examples 1 to 4 were determined for fluorine ion concentration at the temperature condition of thermal cationic polymerization as described below.

<Evaluation of Fluorine Ion Generation of the Complexes>
Each of the complexes (0.2 g) was added to 10 mL of pure water and heated at 100° C. for 10 hours before determining fluorine ion concentration of the supernatant solution with ion chromatography analysis (Dionex Corporation). The obtained results are shown in Table 1. Practically, less than 10 ppm of fluorine ion concentration is desired.

TABLE 1

| Complex | Fluorine Ion Concentration (ppm) |
|---|---|
| Example 1 Sulfonium borate complex (1A) | 2.2 |
| Comparative Example 1 Sulfonium borate complex (1a) | 2.0 |
| Comparative Example 2 Sulfonium borate complex (1b) | 2.3 |
| Comparative Example 3 Sulfonium borate complex (1c) | 2.3 |
| Reference Example 1 Sulfonium antimonate complex (2a) | 165000 |
| Reference Example 2 Sulfonium antimonate complex (2b) | 160000 |
| Reference Example 3 Sulfonium antimonate complex (2c) | 170000 |
| Reference Example 4 Sulfonium antimonate complex (2d) | 172000 |

According to the results in Table 1, the sulfonium borate complexes showed much less amount of generated fluorine ions (less than 10 ppm) than the sulfonium antimonate complexes. From that point of view, the sulfonium borate complex is found to be useful as a thermal cationic polymerization initiator.

Examples 2 and 3, Comparative Examples 4 to 9, Reference Examples 5 to 12

The epoxy resin compositions were prepared by uniformly mixing components in the respective compositions described in Table 2. In addition, each of the epoxy resin compositions was subjected to differential thermal analysis measurement (DSC measurement) and furthermore to the electrolytic corrosion resistance test as described below. It should be noted that the liquid epoxy resin used is Epicoat 828 available from Japan Epoxy Resins. Co. Ltd., the silane coupling agent used is γ-glycidoxypropyltrimethoxysilane (available from Shin-Etsu Chemical Co., Ltd), and the filler used is a spherical fused silica (EB-6D, DENKI KAGAKU KOGYO KABUSHIKI KAISHA).

<DSC Measurement>
The epoxy resin compositions was subjected to differential thermal analysis (exothermic onset temperature, exothermic peak temperature, calorific value) at a heating rate of 10° C./min with a thermal analysis equipment (DSC 5100, Seiko Instruments Inc.). The obtained results are shown in Table 2.

Here, the exothermic onset temperature is a temperature at which protons are generated from the complex to initiate cationic polymerization. Although the lower exothermic onset temperature results in the higher low-temperature fast curing properties, the storage stability tends to be decreased.

Therefore, the exothermic onset temperature of from 60° C. to 80° C. is practically preferable. When the exothermic peak temperature is too low, the storage stability is decreased, whereas when it is too high, curing defects tend to occur. Thus, the exothermic peak temperature of from 100° C. to 110° C. is practically preferable. The calorific value is equal to the heat of the reaction per gram of epoxy resin, and curing defects tend to occur when it is too low. Therefore, the calorific value of 200 J/g or higher is generally desired, although it depends on the epoxy resin used.

<Electrolytic Corrosion Resistance Test (Migration Test)>

The epoxy resin composition to be tested with a thickness of 20 μm was coated on a glass wiring board wherein the glass wiring board has an Al/Cr/ITO electrode or a Mo/ITO electrode on a glass substrate in the form of a comb with 20 μm of gap. The resultant product was then heated at 200° C. for 10 min. to be cured, thereby obtaining a test specimen. The obtained test specimen was placed in a thermostat bath with 85° C. and 85% RH to keep a voltage of 30 V applied between the electrodes for 12 hours. Thereafter, whether discoloration, a defect, a disconnection, and the like occurred in an electrode or not was observed for the front and the back of the glass wiring board under light microscope, and evaluated on the basis of the following criteria. The obtained results are shown in Table 2.

Evaluation Criteria of Electrolytic Corrosion Resistance

G: when discoloration, a defect, a disconnection, and the like were not found.

NG: when discoloration, a defect, a disconnection, and the like were found.

that showed less than 10 ppm of the amount of generated fluorine ions (see Table 1) was used. Based on the DSC measurement in Table 2, the exothermic onset temperature of such compositions was in the range of from 70° C. to 80° C., and the exothermic peak temperature thereof was in the range of from 100° C. to 110° C., and the calorific value thereof was also 200 J/g or more. Therefore, practically satisfactory results were obtained.

In contrast, in the case of the epoxy resin compositions of Comparative Examples 4 to 9 using the sulfonium borate complexes of Comparative Examples 1 to 3, the amount of generated fluorine ions was less than 10 ppm to provide good electrolytic corrosion resistance. There was, however, a problem in the evaluation results of the exothermic onset temperature and the exothermic peak temperature.

Thus, it was found that the sulfonium borate complex of the formula (1A) in Example 1 according to the present invention is superior to other complexes as a thermal cationic polymerization initiator among the sulfonium borate complexes.

In the case of the epoxy resin compositions of Reference Examples 5 to 12 using the sulfonium antimonate complexes (2a) to (2d) of Reference Examples 1 to 4, the amount of generated fluorine ions was more than 100000 ppm, therefore causing a problem in electrolytic corrosion resistance.

INDUSTRIAL APPLICABILITY

When the epoxy resin composition containing the sulfonium borate complex according to the present invention as a thermal cationic polymerization initiator is subjected to thermal cationic polymerization as a thermal cationic adhesive,

TABLE 2

| Formulation of the Epoxy Resin Compositions | Example | | Comparative Example | | | | | | Reference Example | | | | | | | |
|---|---|---|---|---|---|---|---|---|---|---|---|---|---|---|---|---|
| | 2 | 3 | 4 | 5 | 6 | 7 | 8 | 9 | 5 | 6 | 7 | 8 | 9 | 10 | 11 | 12 |
| Liquid Epoxy Resin (parts by mass) | 100 | 100 | 100 | 100 | 100 | 100 | 100 | 100 | 100 | 100 | 100 | 100 | 100 | 100 | 100 | 100 |
| Sulfonium Borate Complex (1A) (parts by mass) | 5 | 5 | | | | | | | | | | | | | | |
| Sulfonium Borate Complex (1a) (parts by mass) | | | 5 | 5 | | | | | | | | | | | | |
| Sulfonium Borate Complex (1b) (parts by mass) | | | | | 5 | 5 | | | | | | | | | | |
| Sulfonium Borate Complex (1c) (parts by mass) | | | | | | | 5 | 5 | | | | | | | | |
| Sulfonium Antimonate Complex (2a) (parts by mass) | | | | | | | | | 5 | 5 | | | | | | |
| Sulfonium Antimonate Complex (2b) (parts by mass) | | | | | | | | | | | 5 | 5 | | | | |
| Sulfonium Antimonate Complex (2c) (parts by mass) | | | | | | | | | | | | | 5 | 5 | | |
| Sulfonium Antimonate Complex (2d) (parts by mass) | | | | | | | | | | | | | | | 5 | 5 |
| Silane Coupling Agent | | 1 | | 1 | | 1 | | 1 | | 1 | | 1 | | 1 | | 1 |
| Filler (Spherical Fused Silica) | | 100 | | 100 | | 100 | | 100 | | 100 | | 100 | | 100 | | 100 |
| <Evaluation Results> | | | | | | | | | | | | | | | | |
| DSC Measurement — Exothermic Onset Temperature (° C.) | 73 | 74 | 85 | 84 | 105 | 103 | 115 | 117 | 73 | 73 | 83 | 84 | 106 | 107 | 116 | 117 |
| DSC Measurement — Exothermic Peak Temperature (° C.) | 103 | 101 | 114 | 112 | 134 | 131 | 147 | 146 | 102 | 101 | 118 | 119 | 135 | 134 | 146 | 147 |
| DSC Measurement — Calorific Value (J/g) | 240 | 230 | 250 | 245 | 320 | 310 | 270 | 280 | 235 | 230 | 290 | 280 | 300 | 310 | 280 | 290 |
| Electrolytic Corrosion Resistance — Al/Cr/ITO | G | G | G | G | G | G | G | G | NG | NG | NG | NG | NG | NG | NG | NG |
| Electrolytic Corrosion Resistance — Mo/ITO | G | G | G | G | G | G | G | G | NG | NG | NG | NG | NG | NG | NG | NG |

In the epoxy resin compositions of Examples 2 and 3, the sulfonium borate complex of the formula (1A) in Example 1 the amount of generated fluorine ions can be reduced to improve electrolytic corrosion resistance and furthermore to provide low-temperature fast curing properties. Thus, the sulfonium borate complex is useful as a thermal cationic polymerization initiator of the epoxy resin composition.

The invention claimed is:

1. An epoxy resin composition comprising an epoxy resin and a thermal cationic polymerization initiator, wherein:

the thermal cationic polymerization initiator is a sulfonium borate complex represented by formula (1):

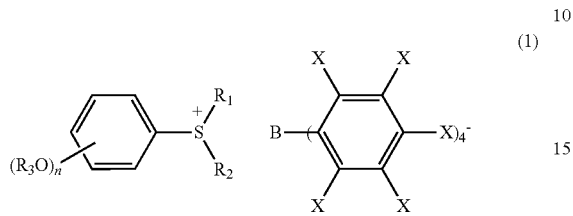

(1)

wherein $R_1$ is an unsubstituted benzyl group, $R_2$ is a methyl group, $R_3$ is bonded to the 4 position of the phenyl group and is a methoxycarbonyl group, X is a fluorine atom, and n is 1; and the epoxy resin composition has an exothermic onset temperature of from 60° C. to 80° C. and an exothermic peak temperature of from 100° C. to 110° C.

2. A connection structure wherein an electronic part is joined to a wiring board with a thermosetting product of the epoxy resin composition according to claim 1.

* * * * *